United States Patent
Hyodo et al.

(10) Patent No.: US 8,269,488 B2
(45) Date of Patent: Sep. 18, 2012

(54) EDDY CURRENT TESTING METHOD, STEEL PIPE OR TUBE TESTED BY THE EDDY CURRENT TESTING METHOD, AND EDDY CURRENT TESTING APPARATUS FOR CARRYING OUT THE EDDY CURRENT TESTING METHOD

(75) Inventors: Shigetoshi Hyodo, Osaka (JP); Satoshi Kureishi, Osaka (JP)

(73) Assignee: Sumitomo Metal Industries, Ltd., Osaka-shi (JP)

( * ) Notice: Subject to any disclaimer, the term of this patent is extended or adjusted under 35 U.S.C. 154(b) by 465 days.

(21) Appl. No.: 12/530,763

(22) PCT Filed: Mar. 11, 2008

(86) PCT No.: PCT/JP2008/054334
§ 371 (c)(1),
(2), (4) Date: Feb. 12, 2010

(87) PCT Pub. No.: WO2008/126553
PCT Pub. Date: Oct. 23, 2008

(65) Prior Publication Data
US 2010/0134099 A1 Jun. 3, 2010

(30) Foreign Application Priority Data
Mar. 14, 2007 (JP) .................................. 2007-064843

(51) Int. Cl.
*G01N 27/32* (2006.01)
(52) U.S. Cl. ........................................................ 324/239
(58) Field of Classification Search .......... 324/219–239, 324/216, 217
See application file for complete search history.

(56) References Cited

U.S. PATENT DOCUMENTS 5,548,214 A * 8/1996 Yasohama et al. ............ 324/240
7,696,747 B2 * 4/2010 Kohama et al. ............... 324/239

FOREIGN PATENT DOCUMENTS

JP 50-26951 9/1975
JP 60-039552 * 3/1985

(Continued)

OTHER PUBLICATIONS

International Search Report in corresponding PCT/JP2008/054334 dated Jun. 17, 2008.

*Primary Examiner* — Patrick Assouad
*Assistant Examiner* — Alesa Allgood
(74) *Attorney, Agent, or Firm* — Marshall, Gerstein & Borun LLP

(57) ABSTRACT

It is an object of the present invention to provide an eddy current testing method capable of securely detecting a high hardness part locally occurring in a metal material having magnetism, and capable of securely checking whether the high hardness part has been removed after execution of a repairing treatment for removing the high hardness part.

In the eddy current testing method according to the present invention, a frequency of the AC current for energizing the differential coil 1 is set so that a phase difference between a magnetism variation signal of the metal material P and a liftoff signal detected by the differential coil is equal to or larger than 135°, and a local high hardness part occurring in the metal material is detected based on an amplitude and a phase of a detection signal outputted from the differential coil.

5 Claims, 2 Drawing Sheets

FOREIGN PATENT DOCUMENTS

| | | | |
|---|---|---|---|
| JP | 60-395552 | | 3/1985 |
| JP | 60-185158 | | 9/1985 |
| JP | 61-277052 | * | 12/1986 |
| JP | 62-030949 | * | 2/1987 |
| JP | 62-174651 | | 7/1987 |
| JP | 11-189844 | | 7/1999 |

* cited by examiner

EDDY CURRENT TESTING METHOD, STEEL PIPE OR TUBE TESTED BY THE EDDY CURRENT TESTING METHOD, AND EDDY CURRENT TESTING APPARATUS FOR CARRYING OUT THE EDDY CURRENT TESTING METHOD

BACKGROUND OF THE INVENTION

1. Field of the Invention

The present invention relates to an eddy current testing method of a metal material such as a steel pipe or tube having magnetism, a steel pipe or tube tested by the eddy current testing method, and an eddy current testing apparatus for carrying out the eddy current testing method. In particular, the present invention relates to an eddy current testing method capable of securely detecting a high hardness part locally occurring in a metal material, and capable of securely checking whether the high hardness part has been removed after execution of a repairing treatment such as grinding for removing the high hardness part, a steel pipe or tube tested by the eddy current testing method, and an eddy current testing apparatus for carrying out the eddy current testing method. Hereinafter, "pipe or tube" is referred to as "pipe" when deemed appropriate.

2. Description of the Related Art

In a production process of a metal material such as a steel pipe, microstructure of the metal material locally changes due to embrittlement of the metal material resulting from microstructure changes such as carburization, decarbonization, deposition of embrittled phase during heat treatment, due to collisions between metal materials or collisions between the metal material and transporting equipment during transportation, or due to a strong working caused by seizure during a cold working. It is known that a local high hardness part arises, and the high hardness part occasionally has a hardness higher than that of the remaining unchanged part, by 50 Hv or larger by Vickers hardness. When such a local high hardness part occurs in a metal material, there arises a fear of breakage due to embrittlement of the metal material and deterioration in corrosion resistance in the high hardness part.

For this reason, it is necessary to detect a local high hardness part occurring in a metal material, and to check whether the high hardness part has been actually removed after execution of a repairing treatment (treatment such as grinding) for removing the high hardness part.

However, detecting a high hardness part and checking removal of the high hardness part by visual inspection, or by using a simplified hardness meter which measures hardness by magnitude of press fit or ultrasonic resonance frequency of an indenter, after press-fitting the indenter into a metal material inconveniently spend time due to difficulty in continuous measurement, and cause variation in determination. Accordingly, if such a local high hardness part can be detected in a non-contact or nondestructive manner, and whether the high hardness part has been actually removed can be checked in a non-contact or nondestructive manner after execution of a repairing treatment for removal of the high hardness part, the efficiency and reliability of detection of high hardness part and checking of removal of high hardness part will be improved.

As a technique of detecting hardness of a metal material or a part where hardness changes in a non-contact or nondestructive manner, for example, Japanese Unexamined Patent Publication No. 58-102148 discloses the art utilizing the fact that the magnetic field having changed due to magnetization of a steel plate (transmitted magnetism) correlates with hardness of the steel plate. Japanese Unexamined Patent Publication No. 59-108970 discloses the art utilizing the fact that magnetic characteristics (coercive force, residual magnetization, saturation magnetization, magnetic permeability, hysteresis loss) of a steel material have correlation with mechanical properties (hardness, burning depth, strength, crystal grain size) of the steel material. Japanese Unexamined Patent Publication No. 60-185158 discloses the art of detecting change in material quality (hardness, carbon content) or nature of a steel pipe using a bridge circuit including a test coil and a comparison coil. Japanese Published Patent Publication No. 9-507570 discloses the art of estimating hardness of steel by measuring a plurality of magnetic parameters of steel.

Japanese Unexamined Patent Publication No. 8-178902 discloses the art of detecting an anomalous microstructure defective part in which a part of surface of a steel plate is carburized and crystal structure is refined, using an eddy current sensor of magnetic saturation type. Japanese Unexamined Patent Publication No. 62-147356 discloses a sigma phase testing method of stainless steel member using an eddy current testing apparatus.

Also Japanese Unexamined Patent Publication No. 2003-232777 discloses a method of detecting an unturned part remaining after a turning process for removing a surface decarbonization layer of steel pipe or round-bar steel occurring due to a heat treatment, by utilizing eddy current.

As described above, it is known that by measuring change in magnetic characteristics of a metal material, for example, by an eddy current testing method, a part where mechanical property such as hardness of the metal material changes can be detected in a nondestructive manner, and the method of checking whether an anomalous part has been removed after a repairing treatment by an eddy current testing method is also known. Therefore, one can conceive of detecting a high hardness part locally occurring in a metal material by using an eddy current testing method, and checking whether the high hardness part has been actually removed by the eddy current testing method after execution of a repairing treatment for removing the high hardness part, by application of the above known arts.

However, when the metal material is a magnetic material, it is sometimes the case that accurate detection of a high hardness part is difficult because a detection signal resulting from magnetism variation (magnetism unevenness) which is inherent to the metal material, and a detection signal resulting from distance (liftoff) variation between the metal material and a detecting coil are superimposed as noises, with respect to a detection signal in the local high hardness part at the time of carrying out an eddy current testing. Further, the region where the high hardness part is removed by grinding or the like shows larger noise signal due to liftoff variation because the surface of the metal material is ground. Therefore, there is a demand for an eddy current testing method capable of detecting a local high hardness part more reliably.

SUMMARY OF THE INVENTION

The present invention was devised to solve the above problems of the conventional arts, and it is an object of the present invention to provide an eddy current testing method capable of securely detecting a high hardness part locally occurring in a metal material having magnetism, and capable of securely checking whether the high hardness part has been removed after execution of a repairing treatment for removing the high hardness part, a steel pipe tested by the eddy current testing method, and an eddy current testing apparatus for carrying out the eddy current testing method.

In order to solve the above problems, inventors of the present invention made diligent efforts and obtained the following findings (1) to (4).

(1) By using a so-called self comparison type differential coil, it is possible to suppress an amplitude of a detection signal resulting from variation in magnetism which is inherent to a metal material (magnetism variation signal), and an amplitude of a detection signal resulting from liftoff variation between the metal material and the differential coil (in particular, detection coil) (liftoff signal).

(2) By adjusting a frequency of an AC current for energizing the differential coil (test frequency), it is possible to adjust a phase difference between the magnetism variation signal and the liftoff signal.

(3) By adjusting the phase difference of the above (2) to be 135° or larger, a phase of the detection signal in a local high hardness part is securely situated between a phase of magnetism variation signal and a phase of liftoff variation signal (a phase of detection signal in the local high hardness part, a phase of magnetism variation signal, and a phase of liftoff signal can be securely distinguished from each other).

(4) Therefore, it is possible to securely detect the high hardness part by using not only the amplitude but also the phase of detection signal outputted from the differential coil after adjustment of test frequency, as information for detecting the local high hardness part locally occurring in the metal material.

The present invention was accomplished based on the above findings found by the present inventors. To be more specific, the present invention provides an eddy current testing method comprising the steps of: energizing a differential coil disposed to be opposite to a metal material having magnetism, with an AC current to make an AC magnetic field act on the metal material, while making the differential coil relatively move with respect to the metal material, and detecting a local high hardness part occurring in the metal material, by detecting an eddy current induced in the metal material by the AC magnetic field with the use of the differential coil, wherein a frequency of the AC current for energizing the differential coil is set so that a phase difference between a magnetism variation signal of the metal material and a liftoff signal detected by the differential coil is equal to or larger than 135°, and a local high hardness part occurring in the metal material is detected based on an amplitude and a phase of a detection signal outputted from the differential coil.

The term "differential coil" used herein means a so-called self comparison type coil in which a detection coil for detecting eddy current is made up of a pair of coils, and difference in detection signals between these coils is outputted. The term "differential coil" used herein includes both a self-induction type coil in which a detection coil also functions as an excitation coil that causes an AC magnetic field to act, and a mutual induction type coil in which a detection coil and an excitation coil are implemented by separate members. The terms "magnetism variation signal" used herein means a detection signal resulting from magnetism variation (magnetism unevenness) which is inherent to a metal material among the detection signals detected by the differential coil. Further, the term "liftoff signal" used herein means a detection signal resulting from variation in distance (liftoff) between the metal material and the differential coil (in particular, detection coil) among detection signals detected by the differential coil.

For example, the local high hardness part to be tested has hardness higher than that of remaining part (normal region in which no local high hardness part occurs) in the metal material by 50 Hv or larger by Vickers hardness.

In order to securely check whether the high hardness part has been removed by a repairing treatment, it is preferred to conduct a repairing treatment for removing a local high hardness part occurring in a metal material, and then to test the metal material with the eddy current testing method, thereby checking whether the high hardness part has been removed.

It is also preferred to conduct a repairing treatment for removing a local high hardness part occurring in the metal material detected by the eddy current testing method, and then to check whether the high hardness part has been removed by retesting the metal material by the eddy current testing method.

The present invention also provides a steel pipe or tube for which removal of the local high hardness part has been tested by the eddy current testing method.

The present invention further provides an eddy current testing apparatus comprising: a differential coil disposed to be opposite to a metal material having magnetism, for inducing an eddy current by making an AC magnetic field act on the metal material, and detecting the eddy current induced in the metal material, and a signal processor for energizing the differential coil with an AC current, and detecting a local high hardness part occurring in the metal material based on a detection signal outputted from the differential coil, wherein the signal processor sets a frequency of the AC current for energizing the differential coil so that a phase difference between a magnetism variation signal of the metal material and a liftoff signal detected by the differential coil is equal to or larger than 135°, and detects a local high hardness part occurring in the metal material based on an amplitude and a phase of a detection signal outputted from the differential coil.

According to the present invention, it is possible to securely detect a high hardness part locally occurring in a metal material having magnetism, and to securely check whether the high hardness part has been removed after execution of a repairing treatment for removing the high hardness part.

DETAILED DESCRIPTION OF THE PREFERRED EMBODIMENTS

In the following, one preferred embodiment of the present invention will be explained with reference to attached drawings as appropriate, for the case where a metal material which is a material to be tested is a steel pipe (duplex stainless steel) having magnetism, as an example.

<Makeup of Eddy Current Testing Apparatus>

Figure 1:
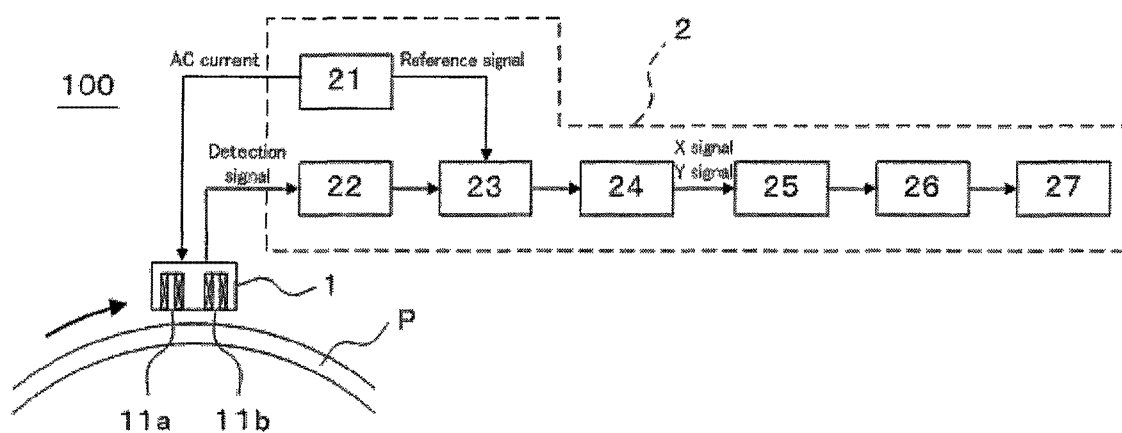
FIG. 1 is a schematic view showing an outline structure of an eddy current testing apparatus according to one embodiment of the present invention.

FIG. 1 is a schematic view showing an outline structure of an eddy current testing apparatus according to one embodiment of the present invention. As shown in FIG. 1, the eddy current testing apparatus 100 according to the present embodiment comprises a differential coil 1 and a signal processor 2.

The differential coil 1 is disposed to be opposite to an outer surface of a steel pipe P for inducing an eddy current by making an AC magnetic field act on the steel pipe P, and detecting the eddy current induced in the steel pipe P. To be more specific, the differential coil 1 according to the present embodiment is a mutual induction type coil in which an excitation coil (not shown) for making an AC magnetic field act on the steel pipe P and a detection coil for detecting eddy current are implemented by separate members. The differential coil 1 according to the present embodiment is a so-called self comparison type coil in which the detection coil is made up of a pair of coils 11a, 11b, and difference in detection signals between these coils 11a, 11b is outputted. The excitation coil makes the AC magnetic field act in the direction perpendicular to the outer surface of the steel pipe P, and the coils 11a, 11b detect change in the AC magnetic field in the direction perpendicular to the outer surface of the steel pipe P occurring due to eddy current. The coils 11a, 11b are disposed while they are spaced from each other in the circumferential direction of the steel pipe P so that when the differential coil 1 is relatively moved in the circumferential direction of the steel pipe P, difference in detection signals about parts of the steel pipe P opposing to the coils 11a, 11b is outputted from the differential coil 1. By using the self comparison type differential coil 1 as described above, it is possible to suppress amplitudes of a liftoff signal and a magnetism variation signal in comparison with the case where a so-called external reference type coil is used.

The signal processor 2 is so configured to energize the differential coil 1 with an AC current, and to detect a local high hardness part occurring in the steel pipe P based on a detection signal outputted from the differential coil 1. Concretely, the signal processor 2 according to the present embodiments has an oscillator 21, an amplifier 22, a synchronous detector 23, a phase shifter 24, a high-pass filter 25, an A/D converter 26 and a determiner 27.

The oscillator 21 supplies the differential coil 1 (concretely, excitation coil of the differential coil 1) with an AC current of predetermined frequency. As a result, as described above, the AC magnetic field directed from the differential coil 1 toward the outer surface of the steel pipe P arises, so that eddy current is induced in the steel pipe P. A setting method of frequency of AC current for energizing the differential coil 1 (test frequency) will be explained later.

The detection signal outputted from the differential coil 1 (concretely, difference in the detection signals between the coils 11a, 11b) is amplified by the amplifier 22, and then outputted to the synchronous detector 23. The amplifier 22 may be so configured to have an AGC (Auto Gain Control) function, as well as to amplify the detection signal at a constant amplification rate.

The synchronous detector 23 synchronously detects an output signal of the amplifier 22 based on a reference signal outputted from the oscillator 21. To be more specific, a first reference signal having the same frequency and the same phase as those of the AC current to be supplied to the differential coil 1, and a second reference signal having a phase shifted by 90° from the phase of the first reference signal are outputted from the oscillator 21 toward the synchronous detector 23. And the synchronous detector 23 separates and extracts, from the output signals of the amplifier 22, a signal component having the same phase as that of the first reference signal (first signal component) and a signal component having the same phase as that of the second reference signal (second signal component). The separated and extracted first signal component and second signal component are respectively outputted to the phase shifter 24.

The phase shifter 24 mutually rotates phases (shifts phases) of the first signal component and the second signal component outputted from the synchronous detector 23 by the same quantity, and outputs, for example, the first signal component as a X signal, and the second signal component as a Y signal to the high-pass filter 25. X signal and Y signal outputted from the phase shifter 24 respectively correspond to components of a signal waveform which is a so-called Lissajous waveform projected to X axis and Y axis in the X-Y vector plane represented by two axes which are perpendicular to each other (X axis, Y axis). The Lissajous waveform is a detection signal waveform of differential coil 1 represented by polar coordinates (Z, θ) wherein Z is amplitude, and phase is θ (accurately, detection signal waveform after amplification by the amplifier 22). Phase rotation by the phase shifter 24 is executed, for example, to adjust the magnetism variation signal be situated on X axis of X-Y vector plane.

The high-pass filter 25 outputs X signal and Y signal outputted from the phase shifter 24 to the A/D converter 26 after removing predetermined low frequency components from these signals.

The A/D converter 26 outputs an output signal from the high-pass filter 25 to the determiner 27 after conducting A/D conversion on the signal.

The determiner 27 is implemented, for example, by a general purpose personal computer in which a program for executing an operation process as will be described later is installed. The determiner 27 detects a high hardness part locally occurring in the steel pipe P based on output data from the A/D converter 26 (namely, digital data obtained by A/D converting X signal and Y signal from which low frequency components are removed by the high-pass filter 25, which are herein after referred to as X signal data and Y signal data). To be more specific, the determiner 27 first calculates amplitude Z and phase θ of detection signal of the differential coil 1 (accurately, detection signal after amplification by the amplifier 22 and removal of low frequency component by the high-pass filter 25) based on the inputted X signal data and Y signal data. Taking value of X signal data as X, and value of Y signal data as Y, amplitude Z and phase θ are respectively calculated according to the following formulas (1) and (2):

$$Z = (X^2 + Y^2)^{1/2} \qquad (1)$$

$$\theta = \tan^{-1}(Y/X) \qquad (2)$$

Then the determiner 27 determines whether the calculated amplitude Z is larger than a predetermined threshold. When the amplitude Z is equal to or less than the predetermined threshold, the determiner 27 determines that the detection signal having this amplitude Z is not a detection signal in a high hardness part. On the other hand, when the amplitude Z is larger than the predetermined threshold, the determiner 27 determines whether the calculated phase θ falls within a predetermined range. When the phase θ falls within the predetermined range, the determiner 27 determines that the detection signal having these amplitude Z and phase θ is a detection signal in a local high hardness part occurring in the steel pipe P (hereinafter, referred to as "high hardness part signal" as appropriate), and outputs a predetermined alarm notifying that a local high hardness part is detected.

<Setting Method of Test Frequency>

In the eddy current testing apparatus 100 having the aforementioned configuration, a frequency of the AC current for energizing the differential coil 1 from the signal processor 2 (oscillator 21) (test frequency) is set so that a phase difference between a magnetism variation signal of the steel pipe P and a liftoff signal detected by the differential coil 1 is 135° or larger. Concretely, a normal region (region in which no local high hardness part occurs) in the steel pipe P is examined by appropriately changing the test frequency, and a test frequency at which difference between a phase of magnetism variation signal of the steel pipe P calculated by the determiner 27 (phase of a magnetism variation signal having maximum amplitude among detected magnetism variation signals) and a phase of liftoff signal (phase of a liftoff signal having maximum amplitude among detected liftoff signals) is equal to or larger than 135° may be selected as a set value.

Hereinafter, the reason why the test frequency is set so that the phase difference between the magnetism variation signal of the steel pipe P and the liftoff signal is equal to or larger than 135° will be concretely explained.

Test examination made by the present inventors revealed the tendency of the phase of a high hardness part signal to be situated between the phase of magnetism variation signal and the phase of liftoff signal. It is also found that when the phase difference between the magnetism variation signal and the liftoff signal is small, the magnetism variation signal and the liftoff signal may be superimposed as noises on the high hardness part signal (the case that a phase of high hardness part signal is similar to the phase of magnetism variation signal or liftoff signal) because the phase of high hardness part signal varies, for example, with the microstructure condition of the high hardness part, and phases of magnetism variation signal and lift signal vary. Accordingly, the present inventors conceived that it is necessary to make the phase difference between the magnetism variation signal and the liftoff signal as large as possible for accurately detecting a high hardness part signal using not only amplitude but also phase as information.

Figure 2:
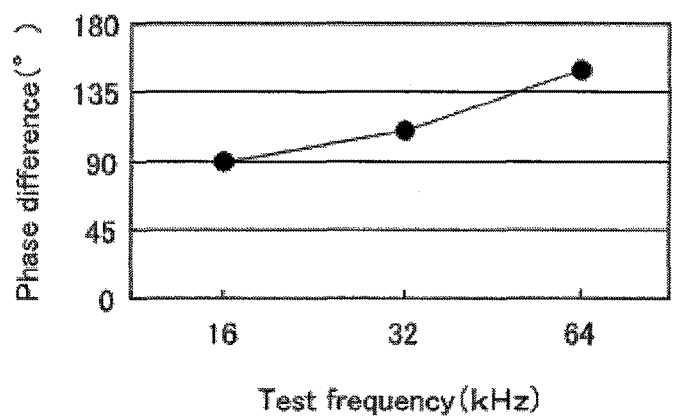
FIG. 2 is a graph showing change in phase difference between a magnetism variation signal of a steel pipe and a liftoff signal detected by a differential coil shown in FIG. 1, when a test frequency is changed.

FIG. 2 is a graph showing change in phase difference between a magnetism variation signal and a liftoff signal of a steel pipe P detected by a differential coil 1 when a test frequency is changed. Examination test made by the present inventors demonstrated that the higher the test frequency, the larger the phase difference between the magnetism variation signal and the liftoff signal becomes as shown in FIG. 2. It is also found that by setting the test frequency so that the phase difference between the magnetism variation signal and the liftoff signal is equal to or more than 135° (in the present embodiment, test frequency is set at 64 kHz), a phase of the high hardness part signal is securely situated between a phase of the magnetism variation signal and a phase of the liftoff variation signal (phase of high hardness part signal, phase of magnetism variation signal, and phase of liftoff signal can be securely distinguishable).

Figure 3:
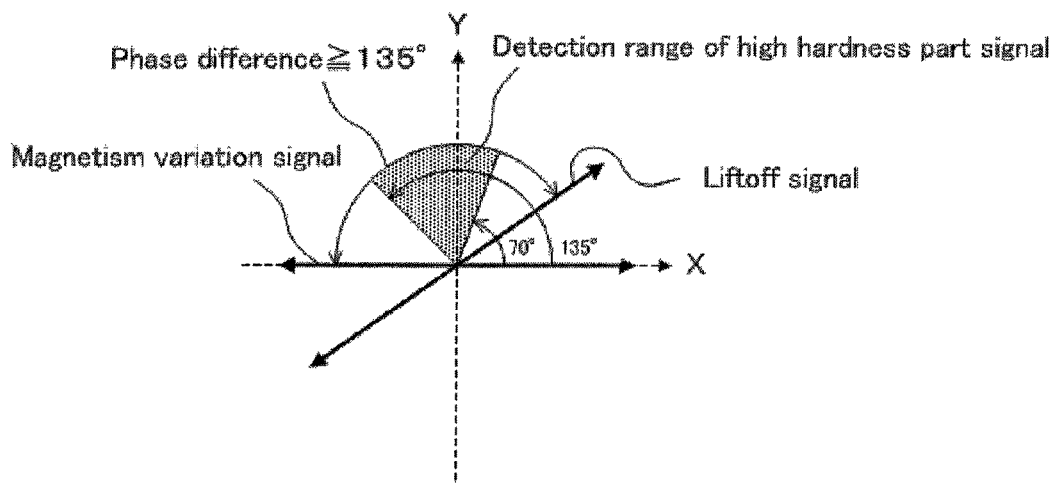
FIG. 3 is a view schematically showing phase relationship between each detection signal (high hardness part signal, magnetism variation signal, liftoff signal) detected by the differential coil shown in FIG. 1.

FIG. 3 is a view schematically showing phase relationship of each detection signal (high hardness part signal, magnetism variation signal, liftoff signal) detected by the differential coil 1. Concretely, FIG. 3 schematically shows directions in which Lissajous waveforms corresponding to respective detection signals calculated based on X signal and Y signal outputted from the phase shifter 24 extend, when the test frequency is 64 kHz. It is also found that, as shown in FIG. 3, when the test frequency is set at 64 kHz, and rotation quantity (phase shift quantity) of the phase shifter 24 is adjusted so that the magnetism variation signal of the steel pipe P is situated on X axis (position at phase of 180°), a phase of the liftoff signal is smaller than 45° (namely, phase difference between the magnetism variation signal and the liftoff signal is equal to or larger than 135°), a phase of the high hardness part signal is detected between the phase of the magnetism variation signal and the phase of the liftoff signal (concretely between phase 70° and 135°). As described above, by setting the test frequency so that the phase difference between the magnetism variation signal and the liftoff signal is equal to or larger than 135°, it is possible to accurately detect the high hardness part signal by the phase difference while the phase of the high hardness part signal does not become comparable to the phase of the magnetism variation signal or liftoff signal.

For the reason as described above, in the signal processor 2, the test frequency is set so that the phase difference between the magnetism variation signal of the steel pipe P and the liftoff signal is equal to or larger than 135° as described above. However, since penetration depth of eddy current changes with change in test frequency (the higher the test frequency, the smaller the penetration depth of eddy current is), it cannot be said that the higher the test frequency the better the result is, and the test frequency is preferably set in consideration of depth of the high hardness part to be tested from the surface of the steel pipe P. Further, when the test frequency is set at excessively high frequency, penetration depth of eddy current is too small, leading the problems that a noise signal is large because of excess sensitivity to convexoconcave on surface of the steel pipe P, and that depth information of the high hardness part is lost. Therefore, it is preferred to set the test frequency while taking these points into consideration.

Figure 4:
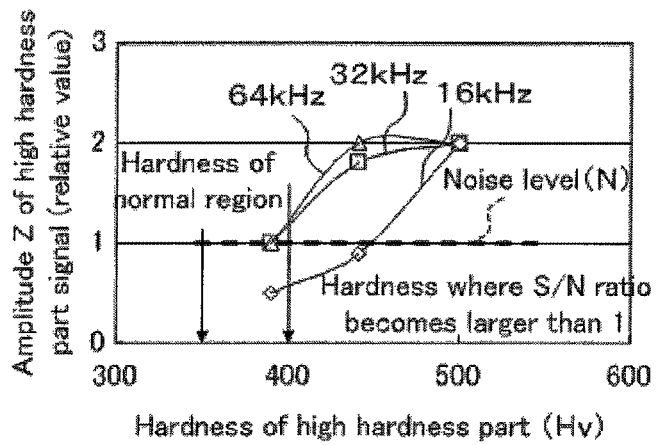
FIG. 4 is a graph showing one example of relationship between hardness of local high hardness part (Vickers hardness) and amplitude of high hardness part signal calculated by a determiner shown in FIG. 1, when the test frequency is changed.

FIG. 4 is a graph showing one example of relationship between hardness (Vickers hardness) of local high hardness part and amplitude of high hardness part signal calculated by the determiner 27 obtained by variable test frequencies of 16 kHz, 32 kHz and 64 kHz. Hardness on the horizontal axis of FIG. 4 means hardness at a depth of 0.1 mm from surface of the steel pipe P. The noise level shown in FIG. 4 means maximum amplitude of a magnetism variation signal or a liftoff signal. As shown in FIG. 4, when the test frequency is set at 64 kHz, eddy current is much concentrated in the vicinity of the surface of the steel pipe P compared to the case where the test frequency is set at 16 kHz, so that the amplitude of the high hardness part signal is large, and the amplitude of the high hardness part signal larger than noise level (namely, S/N ratio of high harness part>1) can be obtained when the high hardness part has hardness higher than hardness of normal region (about 350 Hv) by 50 Hv or larger (namely, having hardness of about 400 Hv or higher). In the present embodiment, as described above, since the test frequency is set at 64 kHz, it is possible to obtain amplitude of high hardness part signal which is larger than the noise level, and to make the phase difference between the magnetism variation signal and the liftoff signal equal to or larger than 135° (make phase of high hardness part signal, phase of magnetism variation signal and phase of liftoff signal securely distinguishable). Therefore, as described above, the determiner 27 determines whether the calculated amplitude Z is larger than a predetermined threshold (for example, noise level), and when the amplitude Z is larger than the predetermined threshold, it is possible to securely detect a high hardness part locally occurring in the metal material by determining whether the calculated phase θ falls within a predetermined range (for example, phase between 70° and 135°).

What is claimed is:
1. An eddy current testing method comprising the steps of:
energizing a differential coil disposed to be opposite to a metal material having magnetism, with an AC current to make an AC magnetic field act on the metal material, while making the differential coil relatively move with respect to the metal material, and detecting a local high hardness part occurring in the metal material, by detecting an eddy current induced in the metal material by the AC magnetic field with the use of the differential coil, wherein a frequency of the AC current for energizing the differential coil is set so that a phase difference between a magnetism variation signal of the metal material and a liftoff signal detected by the differential coil is equal to or larger than 135°, and a local high hardness part occurring in the metal material is detected based on an amplitude and a phase of a detection signal outputted from the differential coil.

2. The eddy current testing method according to claim 1, wherein the local high hardness part has hardness higher than that of remaining part in the metal material by 50 Hv or larger by Vickers hardness.

3. An eddy current testing method comprising the steps of:

detecting a local high hardness part occurring in a metal material having magnetism by the eddy current testing method according to claim 1;

conducting a repairing treatment for removing a local high hardness part occurring in the metal material and then checking whether the high hardness part has been removed by retesting the metal material by the eddy current testing method according to claim 1.

4. An eddy current testing method, comprising the steps of:

conducting a repairing treatment for removing a local high hardness part occurring in a metal material having magnetism;

energizing a differential coil disposed to be opposite to the metal material, with an AC current to make an AC magnetic field act on the metal materials, while making the differential coil relatively move with respect to the metal material;

checking whether the high hardness part has been removed by detecting an eddy current induced in the metal material by the AC magnetic field with the use of the differential coil, wherein a frequency of the AC current for energizing the differential coil is set so that a phase difference between a magnetism variation signal of the metal material and a liftoff signal detected by the differential coil is equal to or larger than 135°, and a local high hardness part occurring in the metal material is detected based on an amplitude and a phase of a detection signal outputted from the differential coil.

5. An eddy current testing apparatus comprising:

a differential coil disposed to be opposite to a metal material having magnetism, for inducing an eddy current by making an AC magnetic field act on the metal material, and detecting the eddy current induced in the metal material, and a signal processor for energizing the differential coil with an AC current, and detecting a local high hardness part occurring in the metal material based on a detection signal outputted from the differential coil, wherein the signal processor sets a frequency of the AC current for energizing the differential coil so that a phase difference between a magnetism variation signal of the metal material and a liftoff signal detected by the differential coil is equal to or larger than 135°, and detects a local high hardness part occurring in the metal material based on an amplitude and a phase of a detection signal outputted from the differential coil.

* * * * *